United States Patent [19]

Bäckström

[11] Patent Number: 5,710,343

[45] Date of Patent: Jan. 20, 1998

[54] METHOD FOR THE PREPARATION OF 3,4-DIHYDROXY-5-NITROBENZALDEHYDE

[75] Inventor: Reijo Johannes Bäckström, Helsinki, Finland

[73] Assignee: Orion-Yhtymä Oy, Espoo, Finland

[21] Appl. No.: 809,405

[22] PCT Filed: Sep. 20, 1995

[86] PCT No.: PCT/FI95/00513

§ 371 Date: May 8, 1997

§ 102(e) Date: May 8, 1997

[87] PCT Pub. No.: WO96/09274

PCT Pub. Date: Mar. 28, 1996

[30] Foreign Application Priority Data

Sep. 23, 1994 [GB] United Kingdom .............. 9419274

[51] Int. Cl.[6] .................................. C07C 37/055
[52] U.S. Cl. ............................... 568/424; 568/426
[58] Field of Search .......................... 568/424, 426

[56] References Cited

U.S. PATENT DOCUMENTS 3,256,336  6/1966  Lange .
5,455,238  10/1995  Aszodi et al. .

FOREIGN PATENT DOCUMENTS 237929    9/1987  European Pat. Off. .
551034    7/1993  European Pat. Off. .
1330382   5/1963  France .
2200109   7/1988  United Kingdom .
93/00323  1/1993  WIPO .

OTHER PUBLICATIONS

F. Hayduck, Versuche zur Darstellung eines Tetraoxyindigos, F. Chem. Ber. 36, Aug. 7, 1903, 2930–2936.

R. L. Burwell, Jr., The Cleavage of Ethers, Chem. Rev. 54, 1954, 615–685.

K.-F. Wedemeyer, II. Phenole durch Umwandlung funktioneller Phenol–Derivate, Methoden der Organischen Chemie (Houben–Weyl), vol 6/1c, 1976, 313–339, 340–358.

M. V. Bhatt et al., Cleavage of Ethers, Synthesis, 1983, 249–282.

Primary Examiner—Gary Geist
Assistant Examiner—Sreeni Padmanabhan
Attorney, Agent, or Firm—Finnegan, Henderson, Farabow, Garrett, and Dunner, L.L.P.

[57] ABSTRACT

The invention provides a method for the preparation of 3,4-dihydroxy-5-nitrobenzaldehyde by reacting 3-ethoxy-4-hydroxy-5-nitrobenzaldehyde with a reagent comprising zinc chloride, water and hydrogen chloride.

10 Claims, No Drawings

METHOD FOR THE PREPARATION OF 3,4-DIHYDROXY-5-NITROBENZALDEHYDE

This is the US National Stage Application of PCT/FI95/00513 filed Sep. 20, 1995 now WO96/09274 Published Mar. 28, 1996.

The invention relates to a new method for the preparation of 3,4-dihydroxy-5-nitrobenzaldehyde, which is an important intermediate in the synthesis of several pharmaceutically important compounds having 5-substituted 3-nitrocatechol structure, e.g. entacapone.

All known methods for the preparation of 3,4-dihydroxy-5-nitrobenzaldehyde are based on demethylation of 4-hydroxy-3-methoxy-5-nitrobenzaldehyde. The oldest method (Hayduck, F. Chem. Ber. 36 (1903), p. 2930) uses hydrochloric acid as the reagent. The method is inapplicable because the starting material and/or the product decomposes during the process, which decreases the yield. The process also produces an impure product (mp: 106° C.) and the reaction must be performed under pressure.

An improved method is described in EP 237929 and GB 2200109. This method uses hydrobromic acid in stead of hydrochloric acid. A specific problem with this method is the formation of a ring brominated impurity (probably 2-bromo-3,4-dihydroxy-5-nitrobenzaldehyde) and of an unspecified brownish black impurity. Further, this method and the above mentioned hydrochloric acid based method share the common problem that pushing the reaction to completion highly increases the amount of impurities. If the demethylation is not performed to completion the 3,4-dihydroxy-5-nitrobenzaldehyde produced contains some 4-hydroxy-3-methoxy-5-nitrobenzaldehyde. This impurity is very difficult to remove and therefore makes the 3,4-dihydroxy-5-nitrobenzaldehyde poorly suitable for further processing.

The third method has been described in the PCT patent application WO 93/00323. It is based on dealkylation using the combination of lithium hydroxide and thiophenol or 2-mercaptobenzothiazole in a polar aprotic solvent. This procedure does not have the problems associated with the decomposition of the product in the reaction medium, so the reaction can be pushed to completion. The method makes it possible to prepare pure 3,4-dihydroxy-5-nitrobenzaldehyde, but it still has many problems which make its large scale industrial utilisation difficult. First, the organic reagent and the expansive lithium hydroxide are consumed during the reaction, so they are not recyclable. Secondly, the process necessitates the use of a polar aprotic solvent together with an another organic solvent and water. During the recycling of the solvents a method is needed to separate the two organic solvents from each other and also to get the polar aprotic solvent dry enough for further use.

This invention is based on the surprising observation, that 3-ethoxy-4-hydroxy-5-nitrobenzaldehyde may be cleaved by a reagent containing zinc chloride, water and hydrogen chloride to form 3,4-dihydroxy-5-nitrobenzaldehyde. It is surprising to be able to use zinc chloride as the Lewis acid to facilitate dealkylation reaction even though it is known that alkyl aryl ethers can be cleaved using a Lewis acid (Bhatt, M. V. and Kulkarni, S. U., Synthesis (1983), p. 249; Burwell, R. L. Chem. Rev. 54 (1954), p. 615; K. F. Wedemeyer in Methoden der Organischen Chemie (Houben-Weyl), Vol 6/1c, pp. 340–358, Georg Thieme Verlag, Stuttgart 1976).

It is also exceptional, that the reaction may be carried under aqueous conditions. The method described here is specific for 3-ethoxy-4-hydroxy-5-nitrobenzaldehyde and it is not applicable to 4-hydroxy-3-methoxy-5-nitrobenzaldehyde, which is practically inert under the conditions used. This finding is surprising, because an ethoxy group is reported to have low reactivity compared to a methoxy group in common acid catalyzed dealkylation (K. F. Wedemeyer in Methoden der Organischen Chemie (Houben-Weyl), Vol 6/1c, p. 314, Georg Thieme Verlag, Stuttgart 1976).

The present process is simple and the reagents are cheap and easily recyclable. Further, a high purity product is obtained because the residual starting material, 3-ethoxy-4-hydroxy-5-nitrobenzaldehyde, is easily removed by one crystallization. The reaction may be carried out in water; an organic solvent is not necessary. The only reagent consumed during the process is hydrogen chloride. After the reaction the product is isolated by diluting the mixture with water and filtering the product. The product may be further purified by crystallization using conventional organic solvents, preferably toluene. The zinc chloride can be recovered from the filtrate by evaporation to dryness. Before evaporation it is advantageous to extract the filtrate with an organic solvent such as ethyl acetate to remove organic impurities. It is also possible to melt the zinc cloride after evaporation, this process destroys organic impurities.

The process is successful when performed using the following conditions: The amount of zinc chloride is preferably from 1.5 kg to 25 kg per 1 kg of 3-ethoxy-4-hydroxy-5-nitrobenzaldehyde, most preferably from 2.5 kg to 4 kg. The amount of the hydrochloric acid is preferably from 0.17L to 0.6L per 1 kg of zinc chloride, most prefererably from 0.22L to 0.4L. The concentration of the hydrochloric acid to be added to the reaction mixture is preferably from 10% to 40%, most prefererably between 20% to 38%. The temperature is preferably from 70° C. to 130° C., most prefererably from 80° C. to 110° C.

THE PREPARATION OF THE STARTING MATERIAL

3-Ethoxy-4-hydroxy-5-nitrobenzaldehyde: Fuming nitric acid (22.0 mL) was added (rate approx. 1.5 mL/min) to a stirred solution of 3-ethoxy-4-hydroxybenzaldehyde (83.0 g) in dichloromethane (400 mL) at 5°–10° C. Thereafter the mixture was stirred for 30 min at 3° C. and then filtered. The product was washed with dichloromethane and water and dried in vacuo at 50° C., yield 77.8 g (73,7%).

THE EXAMPLE 3,4-Dihydroxy-5-nitrobenzaldehyde: A mixture of 3-ethoxy-4-hydroxy-5-nitrobenzaldehyde (20.0 g), zinc chloride (60.0 g) and hydrochloric acid (37%, 15 mL) was stirred at 90° C. for 17 h. The mixture was diluted with water (100 mL) and then cooled to 3° C. After 1 h the product was filtered and washed with cold water. The product was dried in vacuo at 100° C. to give 16.5 g (95.1%) of crude product. The crude product was mixed with toluene (275 mL) and activated carbon (2,0 g) and the resulting mixture was refluxed for 45 min. The hot solution was filtered and then cooled to 3° C. After 1 h the product was filtered and washed with cold toluene. It was dried in vacuo at 50° C. to give 12.6 g (72.6%) of pure 3,4-dihydroxy-5-nitrobenzaldehyde (mp. 146°–8° C.).

I claim:

1. A method for the preparation of 3,4-dihydroxy-5-nitrobenzaldehyde characterized in that 3-ethoxy-4-hydroxy-5-nitrobenzaldehyde is reacted with a reagent comprising zinc chloride, water and hydrogen chloride.

2. The method according to claim 1, characterized in that the amount of zinc chloride is from 1.5 kg to 25 kg per 1 kg of 3-ethoxy-4-hydroxy-5-nitrobenzaldehyde.

3. The method according to claim 2, characterized in that the amount of zinc chloride is from 2.5 kg to 4 kg per 1 kg of 3-ethoxy-4-hydroxy-5-nitrobenzaldehyde.

4. The method according to claim 1, characterized in that the amount of the hydrochloric acid is from 0.17L to 0.6L per 1 kg of zinc chloride.

5. The method according to claim 4, characterized in that the amount of the hydrochloric acid is from 0.22L to 0.4L per 1 kg of zinc chloride.

6. The method according to claim 1, characterized in that the concentration of the hydrochloric acid is from 10% to 40%.

7. The method according to claim 6, characterized in that the concentration of the hydrochloric acid is from 20% to 38%.

8. The method according to claim 1, characterized in that the temperature is from 70° C. to 130° C.

9. The method according to claim 8, characterized in that the temperature is from 80° C. to 110° C.

10. The method according to claim 1, characterized in that the crude product is further crystallized from toluene.

* * * * *